United States Patent [19]

DuBrucq et al.

[11] Patent Number: 4,502,487
[45] Date of Patent: Mar. 5, 1985

[54] OPTICAL THERMODETECTOR

[76] Inventors: Denyse C. DuBrucq, 1520 17th St. North, #4, Arlington, Va. 22209; Henry C. Kondracki, 707 Tamarack Way, Herndon, Va. 22070

[21] Appl. No.: 490,045

[22] Filed: Apr. 29, 1983

[51] Int. Cl.³ ............................................. A61B 5/00
[52] U.S. Cl. .................................... 128/665; 128/736; 128/737; 128/738
[58] Field of Search ................................. 128/633–634, 128/664–665, 736–738; 374/112, 124, 137, 142

[56] References Cited

U.S. PATENT DOCUMENTS

| | | | |
|---|---|---|---|
| 1,928,278 | 3/1932 | Zelov | 116/114 |
| 2,686,908 | 12/1952 | Amundson et al. | 340/227 |
| 3,529,568 | 9/1970 | Quin | 116/114.5 |
| 3,583,389 | 6/1971 | Harvey | 128/2 |
| 3,633,425 | 1/1972 | Sanford | 128/736 |
| 3,871,232 | 3/1975 | Pickett et al. | 374/112 |
| 4,070,912 | 1/1978 | McNaughtan et al. | 374/112 |
| 4,148,304 | 4/1979 | Mull | 128/2 R |
| 4,151,831 | 5/1979 | Lester | 128/736 |
| 4,269,192 | 5/1981 | Matsuo | 128/665 |
| 4,280,508 | 7/1981 | Barrada | 128/736 |
| 4,290,433 | 9/1981 | Alfeno | 128/665 |
| 4,396,020 | 8/1983 | Wolff et al. | 128/738 |
| 4,402,311 | 9/1983 | Hattori | 128/736 |

FOREIGN PATENT DOCUMENTS 2447707 10/1980 France ................................. 128/736

Primary Examiner—William E. Kamm
Assistant Examiner—Mitchell J. Shein
Attorney, Agent, or Firm—Armstrong, Nikaido, Marmelstein & Kubovcik

[57] ABSTRACT

An optical thermodetector for in vivo testing of tissue is disclosed which has a housing including a case and a needle-like extension projecting therefrom, the extension having a sharp end for piercing the skin of a patient, a temperature element disposed within the housing and having indicating means responsive to a predetermined change in temperature, and an optical element disposed within the housing for recording coloration of tissue. The recording of coloration of tissue takes place as the extension is withdrawn from a depth within the skin of a patient. The recordation on film of the coloration of the tissue corresponds to the recordation of the temperature.

16 Claims, 7 Drawing Figures

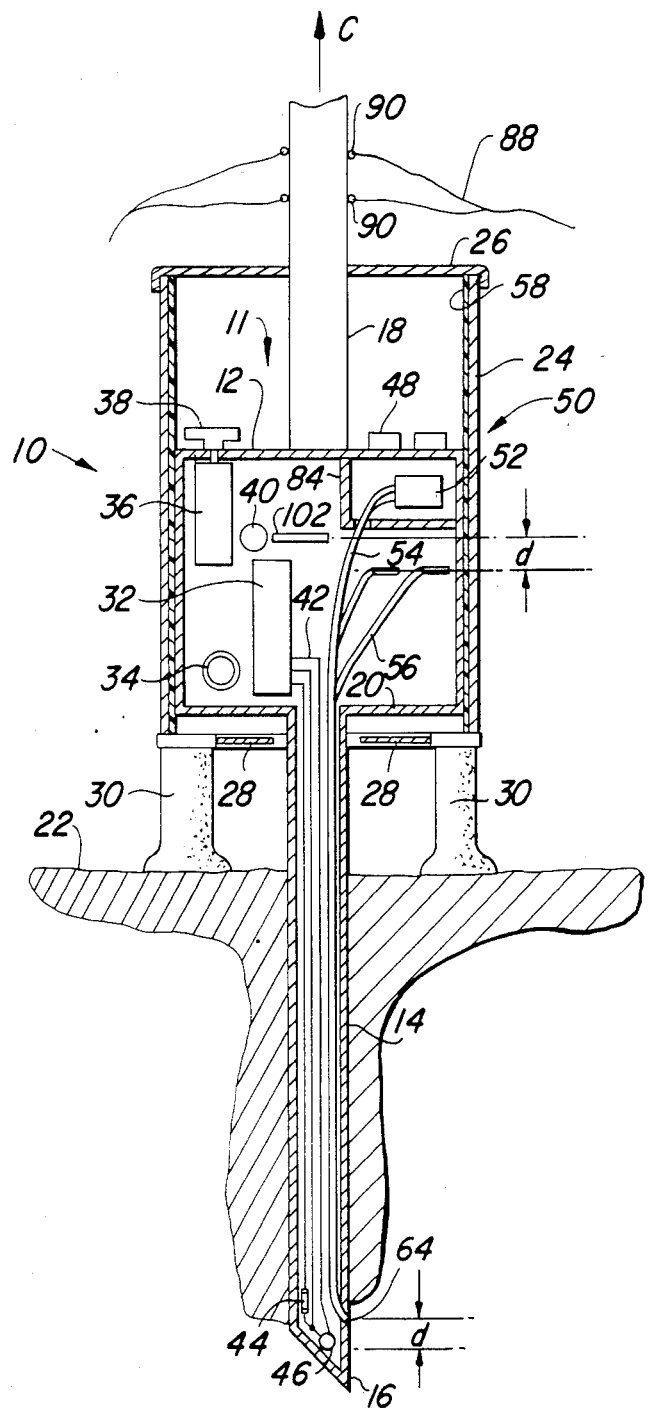
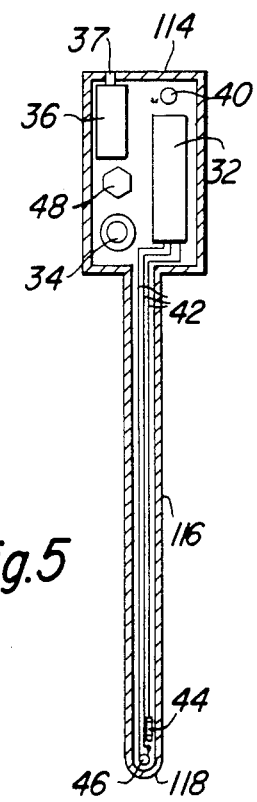

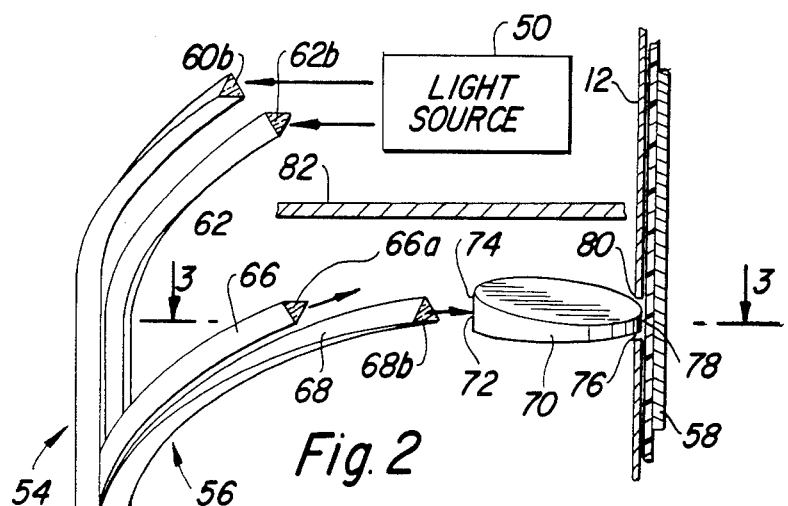
Fig. 2
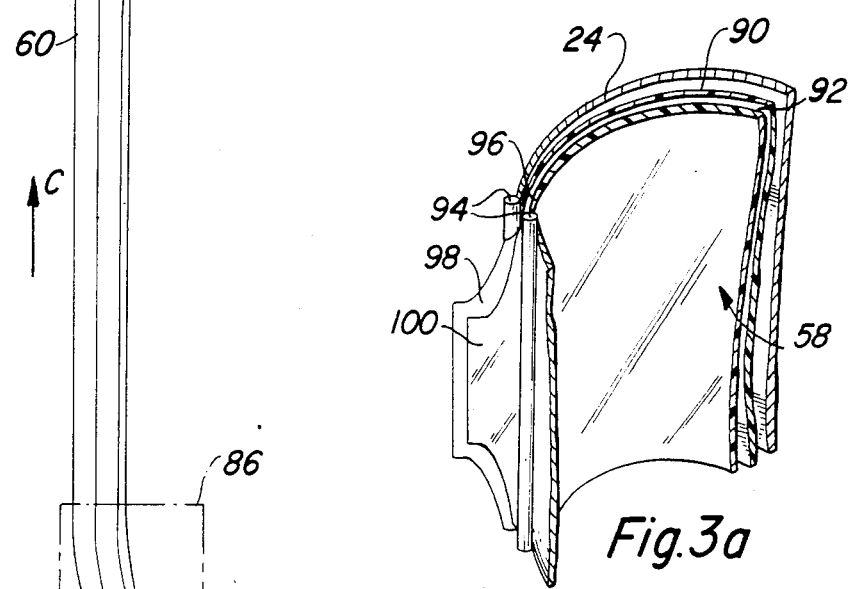
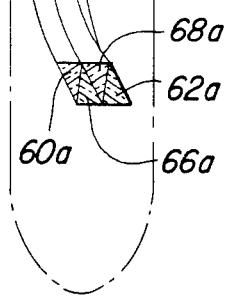
Fig. 3
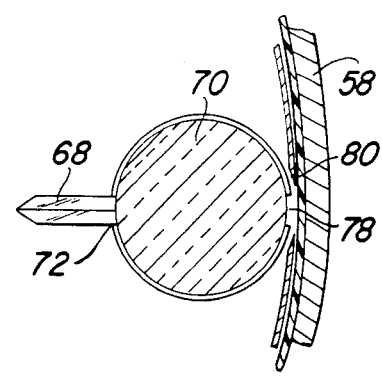
Fig. 3a

OPTICAL THERMODETECTOR

BACKGROUND OF THE INVENTION

The optical thermodetector of the instant invention relates generally to devices for in vivo testing of tissue. The instant invention provides for an optical recording of temperature and tissue color at the point of testing. One application for the device is to give indication if a tissue is malignant, because malignant tissues frequently exhibit a different basal temperature than surrounding normal tissue in warm blooded animals, including man and frequently have coloration differences from normal tissue. This means of in vivo sampling could prevent the need for a painful biopsy in many situations where the information from the instant optical thermodetector will suffice for diagnosis.

The instant thermodetector may also be used to aid women in birth control. It is well known that unwanted pregnancies can be avoided through abstention from intercourse during ovulation and for a period immediately thereafter. This is, of course, dependent upon knowing the time of ovulation. This is often accomplished by temperature charting, which is a method consistent with sympto-thermal methods of family planning now in wide use today. This temperature determination allows a woman to know when she reaches the critical day in fertility, ovulation, which is indicated by a 0.4° F. rise in her basal temperature. The rise in temperature occurs when a woman's progesterone production is stimulated by hormones released from the corpus luteum following the release of the egg cell from the ovary. The normal lower basal temperature occurs when estrogen, not progesterone, is a dominating hormone.

SUMMARY OF THE INVENTION

The instant optical thermodetector provides for a device to efficiently explore tissue in vivo. This device combines both temperature and color sensors in a probe or a needle like extension designed to be inserted in the tissue to be tested. When this device is inserted into the tissue of a patient it combines a determination of temperature differences to 0.1° F. (with accuracy to 0.01° F.) and monitors coloration changes of tissue along the probe (or needle or extension) path as it is withdrawn from the tissue. The thermal and optical information obtained while the probe is being withdrawn from the tissue is then recorded on film disposed within a housing attached to the probe. The shape of the probe will generally be cylindrical and its diameter could vary from just larger than an acupuncture needle to any size necessary. However, the needle length will vary according to the distance of the tissue to be observed below the surface. Longer probes would be used for the thigh or torso than for the arm or tissues estimated to be close to the surface.

The optical thermodetector of the instant invention comprises: a housing including a case and a needle like extension projecting therefrom, said extension having a sharp end for piercing the skin and tissue of a patient; a temperature element disposed within said housing and having indicating means responsive to a predetermined change in temperature; and optical element disposed within said housing for recording the coloration of tissue.

The optical element of the instant optical thermodetector generally includes a light source, an incident light path for conducting light from said light source to the tissue to be tested, a light collector located within the case, a film plane where film for recording tissue coloration is to be located, the film plane being movable with respect to the light collector, and a reflected light path for conducting reflected light from the tissue to the light collector for projection onto a film plane. The film plane is generally located in a cylindrical cartridge fitting over the case which contains many of the elements of the optical thermodetector. This cartridge is slidable axially with respect to the case so that light emitted by said light collector may be projected onto the film plane as it is traveling upward with respect to the case.

The temperature element may also be equipped with a light emitting diode (LED) indicator glowing when at or lower than a preset temperature and dark when higher than the preset temperature. The incident light path from the light source to the tissue and the reflected light path from the tissue to the light collector are ideally composed of optical fibers having a triangular cross section. The reflected light is then conducted from the light fibers to the light collector which in turn projects the light onto the film plane. Therefore both the LED of the temperature element and the optical fibers, carrying the reflected light from the tissue tested through the light collector, are transmitting light to the film plane. Then as the extension or needle is withdrawn slowly from the puncture sight on the patient, the case, connected with said extension moves with respect to the film plane thus recording the temperature change through the illumination of the LED and the skin coloration through the optical fibers, and light collector, on film disposed in the film plane. Small slits in the case will allow the light to be projected from inside the case onto the film. The film will then show tissue color, the interfaces between tissue types, and temperature of that tissue as plus or minus a reference temperature. This is easily done by reading across the columns of color from the optical fibers and the light and dark from the LED indicator of temperature on the resultant photograph.

It is additionally contemplated that the temperature element may be used without the optical element. Such a device using only the temperature element would be effective for determining the time of ovulation in a woman's fertility cycle. For those women with a basal temperature record showing a constant ovulation temperature over several months observation using the sympto-thermal method, ovulation can be determined with the temperature element preset for the ovulation temperature. Temperature should be taken in a consistent and exact location, generally either orally, vaginally, or rectally, after sleep and prior to rising daily during the high mucus stage of the female cycle until ovulation. With ovulation indicated, temperature monitoring can then await the next mucus phase of the cycle.

The temperature element employed includes a means for setting a reference temperature, means for detecting a predetermined change in temperature from the reference temperature, and means operatively connecting the detecting means with the indicating means for energizing the indicating means in response to the predetermined change in temperature. For example, an LED operating as the indicating means would be illuminated when the woman's basal temperature is below that of ovulation. When the LED goes off after the insertion of the temperature element, it indicates that ovulation temperature is reached. The reference temperature should be set by a qualified physician or technician at the woman's normal basal temperature.

It is also contemplated that such a temperature element could be used in triplicate. That is, in a single housing, three temperature elements would be included, each having slightly different reference temperature. The use of the three reference indicators, rather than one, allows a more complete identification the female ovulation cycle. A couple could keep track of the chart location for each cycle if the temperature where taken daily during the high mucus phase of the cycle. Abstinence at the onset of the mucus period until four days following ovulation is a proven and reliable means of preventing conception.

The three temperatures to be set, each with its own color LED, could be the estrogen based basal temperature averaging that over the larger section of the cycle, 0.1° F. below the ovulation temperature, and the ovulation temperature, which in most women is 0.4° F. above the basal temperature for the rest of the female cycle. Where, for example, the LED colors are green, yellow, and red, respectively, with all LED's glowing when taking the temperature, the basal temperature can be below the normal basal temperature of the woman. This is not an uncommon occurrence. Where the green LED is out and only the yellow and red LEDs are on, ovulation has not occurred. Where only the red LED is glowing ovulation may be in progress, but with not sufficient progesterone produced to fully raise the temperature to 0.4° F., or it may be one or two days after ovulation. If the following day all LEDs go out, ovulation has occurred. Once the device is removed from the orifice where the temperature is taken, and cools, all LEDs should once again be on. If this does not occur then the reading is not valid and the batteries should be checked.

BRIEF DESCRIPTION OF THE DRAWINGS

In the drawings:

FIG. 1 is a cutaway view of the optical thermodetector of this invention;

FIG. 2 is a partial exploded view of portions of the optical element shown in FIG. 1;

FIG. 3 is a plan view taken along line 3—3 of FIG. 2;

FIG. 3a is a partial cutaway view of the cartridge of FIG. 1;

FIG. 5 is a cut away view of a second embodiment of the instant invention; and

DETAILED DESCRIPTION OF THE INVENTION

Figure 4:
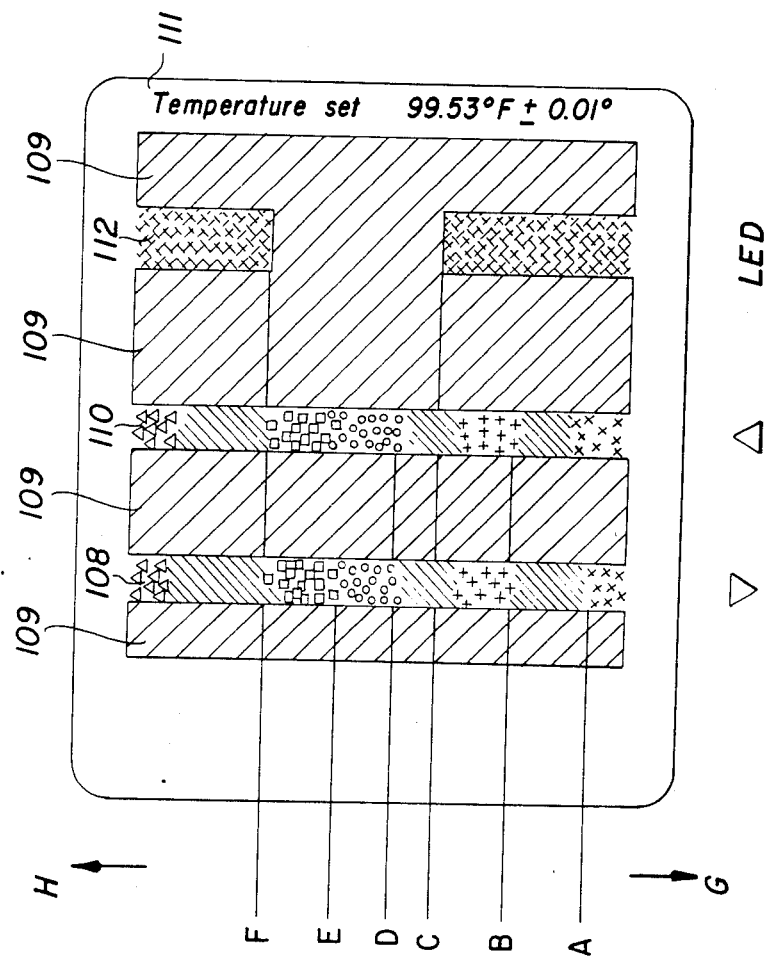
FIG. 4 is a diagrammatical representation of a resulting photograph from the optical thermodetector of FIGS. 1-3.

Referring to FIG. 1, the optical thermodetector 10 of the instant invention is disclosed having a case 12 with an extension or needle 14 projecting therefrom. Needle 14 has a sharp end 16 for piercing the skin of the patient. Case 12 is a generally cylindrical shape having a rod 18 extending upwardly from the top thereof, and needle 14 fixed at the lower portion thereof at point 20. Rod 18 has a removable handle (not shown) for withdrawing the needle 14 from within the patient. Surrounding the case 12 is cartridge 24, which is generally cylindrical in shape and fits very snuggly over case 12. Case 12 and cartridge 24 are axially shiftable with respect to each other. Cartridge 24 has a removable light-tight seal 26 at its upper portion which surrounds rod 18. At its lower end cartridge 24 has a light-tight diaphragm type shutter 28 which is manually operable for closure upon the removal of needle 14 and case 12 from within cartridge 24. Upper seal 26 on cartridge 24 may be removed for the total withdrawal of the instrument assembly 11 (which includes rod 18, case 12 and needle 14) from the cartridge 24. Below shutter 28 is a cylindrical collar 30 which is preferably composed of a light-tight foam type material to maintain a light-tight seal between the optical thermodetector 10 and the skin of the patient 22. The area designated as 23 generally relates to the tissue of the patient below the skin 22. The foam of collar 30 will be flexible enough so that extension 14 may be inserted into the patient's skin at an angle and still maintain the light-tight seal.

Inside of case 12 is a temperature element comprised mainly of electronics module 32, battery 34, variable resistor 36 with its adjustment knob 38, LED indicator 40, and wires 42 connecting the electronics module with resistor 44 and thermistor 46. The variable resistor 36 operates as a means for setting a reference temperature used in the operation of this optical thermodetector. Resistor 44 and thermistor 46 form the temperature sensor element which will sense a change in temperature from the reference temperature. Electronics module 32 provides the required circuit to energize or deenergize LED 40 upon the detection of the preset change in temperature. Switch 48 switches power to the temperature element. Resistor 44 and thermistor 46 are located at the extremity of needle 14 near its end 16. The actual operation of the circuitry of electronics module 32 will be described in detail in the description of the second embodiment, below.

Standing side by side with the temperature element of the optical thermodetector 10 is the optical element as generally indicated by the reference numeral 50. The optical element 50 generally includes a light source 52, an incident light path 54, a reflected light path 56, and a film plane 58 which is located around the interior of the cylindrical cartridge 24 for holding the film when an exposure is made.

Referring now to FIG. 2, in addition to FIG. 1, incident light path 54 is composed of two optical fibers 60 and 62 which extend from light source 52 near the top of the case 12 down along the length of needle 14 to a point 64 near the end 16 of needle 14 where the fibers are terminated such that the light is then projected outwardly onto the tissue to be tested. Optical fibers 66 and 68 make up the reflected light path 56. These fibers conduct reflected light from the tissue which enters generally at point 64 and is conducted up the length of fibers 66 and 68 to be projected through a focusing lens 70 onto the film plane 58. In FIG. 2 fiber 68 is shown projecting light onto lens 70. In actual operation face 68b of fiber 68 will be mounted on lens 70 at point 72. Likewise fiber 66 will project its light into a lens similar to lens 70 (not shown for clarity of the drawing) in a like manner. Lens 70, as can also be seen in the top view of FIG. 3, is a generally disc-like shape being relatively thick at the input edge 74 and relatively thin at the output edge 76. Lens 70 has an opaque coating covering it, except for an aperature located at point 72 for receiving light from fiber 68 and aperature 78 for projecting the light conducted through optical fiber 68 onto adjacent film plane 58. Light source 52 is in a light-tight compartment 84 so that light will not spill over from the light source into unwanted areas and unintentionally expose the film. Light tight compartment 84 is represented schematically by barrier 82 in FIG. 2. Note that in FIG. 2 the end of needle 14 is represented by reference numeral 86 in phantom. Ends 60a and 62a project light from fibers 60 and 62 to the tissue to be tested. The light exits at ends 60a and 62a, reflects off the adjacent tissue and is reflected into ends 66a and 68a of fibers 66 and 68. The reflected light is then conducted up the fibers to be projected eventually onto film plane 58. It should be noted that fibers 60, 62, 66, and 68 are all light insulated from each other.

It should be noted that shroud 88 contains two elastic members 90 to maintain a double light seal around rod 18. Shroud 88 will completely cover the optical thermodetector and also cover the immediate area of the patients skin surface 22, although the extent of coverage of shroud 88 is not shown for simplicity of the drawing.

While FIG. 2 discloses a fiber bundle of four different fibers, incident fibers 60 and 62 and reflected fibers 66 and 68, the device of this invention also contemplates the use of multiple bundles of fibers. These fibers could be arranged circumferentially around the circumference needle 14 to form a more complete picture of the tissue surrounding the needle rather than just on one side. However, it is important that any increase in the number of optical fibers used will be in bundles of four fibers each, each of the fibers having a triangular cross-section. As seen in FIG. 2, the fiber ends 60a, 62a, 66a, and 68a in the tip of needle 14 are bundled together to form nearly a parrallelogram type bundle. Each of the outer fibers, 60a and 62a transmit light from the light source onto the tissue to be tested. Inner ends 66a and 68a receive the reflected light from the tissue and conduct that reflected light along fibers 66 and 68 to be eventually projected onto the film located on the film plane 58. It should be noted that the upper most edge, or base 168, of triangular end 68a is adjacent to the upper most tip 166 of triangular end 66a. Accordingly, the lower most base of end 66a is adjacent the lower most tip of end 68a.

As needle 14 is withdrawn from old tissue to new tissue, base 168 of fiber 68 and tip 166 of fiber 66 cross an interface between layers of tissue simultaneously. As end 68a and 66a are halfway across such an interface, fiber 68 transmits much more of the color from the new layer than fiber 66. This is because the area for receiving light is greater because base 168 crosses the interface first. Fiber 66 transmits more of the color of the old layer, because the major portion of end 66a is still receiving light from the old layer of tissue, as only tip 166 is in the new layer. Therefore the interface between the old layer and new layer of tissue is indicated by a rapid change in color transmitted from fiber 68.

FIG. 3a shows cartridge 24 in the cutaway view without top seal 26 and its lower portion including diaphragm shutter 28, film plane 58 is shown containing film 90 and film cover 92. The purpose of film cover 92 is to keep the film 90 from being exposed while the cartridge is being loaded and is being prepared for use in the optical thermodetector. Rollers 94 are located just outside slit 96 and extend longitudinally along the length of cartridge 24. Slit 96 extends the length of cartridge 24 also, and is light-tight along its length and at each end. Tabs 98 and 100 project out from the slit 96 and are attached to film 90 and film cover 92 respectively. Developing rollers 94 extend the length of cartridge 24 (although the bottom is not shown in FIG. 3a). These rollers initiate the developing of the film, when instant developing film is used, after it has been exposed, when it is pulled through the rollers. Film cover 92, of course, is removed by pulling tab 100 before exposure of the film.

The description of the operation of the electronics module 32 in conjunction with the battery 34, variable resistor 36, LED 40, resistor 44 and thermistor 46 will be described in detail below. In operation, however, a reference temperature is set by adjusting the knob 38 of variable resistor 36. At this point of reference the LED will remain illuminated. When the temperature sensed by resistor 44 and thermistor 46 changes by a predetermined amount (for example 0.1° F.) the LED will turn off. This will be the basis of recording the temperature on the film by the exposure of the film from the LED 40 through slit 102 as shown in FIG. 1. A lens may or may not be employed between LED 40 and slit 102.

In operation, the optical thermodetector of the instant invention functions as follows: First the film needs to be prepared and inserted into cartridge 24. Film may be either instant developing type or the standard film in use. This description will describe the invention using instant developing film. As seen in FIG. 3a, film 90 is placed on the inside of cartridge 24, preferably only one frame at a time. The film may come with, or it may be additionally provided with, a film cover 92 which covers the film to keep it from being exposed inadvertently. Developing rollers 94 extend longitudinally along the side of cartridge 24 and are disposed immediately outside of light-tight slit 96. The tabs 98 and 100 of film 90 and film cover 92 respectively project from the interior of the cartridge 24 outward through rolls 94. So long as cover 92 remains in place, film 90 will not be exposed, inadvertently or otherwise.

Once the patient has been prepared and the place for insertion of the needle has been prepared, the needle is inserted into the patient to the proper depth. The tissue is then ready to be scanned, as the needle is withdrawn from within the patient. After the needle is inserted to the desired depth, the temperature element is turned on by switch 48. Additionally, switch 104 is turned on which illuminates light source 52. Then the variable resistor 36 is adjusted by using knob 38 to the temperature of the tissue in which it is embedded so that the LED is glowing but a 0.1° F. temperature raise will cause it to turn off. Once these initial adjustments have been made, the instrument assembly 11 is ready to receive the cartridge 24 around it. While rod 18 has a removable handle (not shown) the handle will be removed in order to let the cartridge 24 with top seal 26 fit down over rod 18 and over case 12. Cartridge 24 is fitted such that collar 30 rests upon the skin of the patient while forming a light-tight seal around the needle. Diaphragm type shutter 28 may be manually adjusted such that it is closely fit around needle 14. A light-tight seal between shutter 28 and needle 14 is not necessary at this time. Once the needle 14 is withdrawn completely, shutter 28 will be closed completely to provide a light-tight seal.

Once the needle is in position and the cartridge 24 is in position over the case 12, shroud 88 should be fitted down on top of rod 18, the outer periphery of shroud 88 (not shown) will be extended well around the optical thermodetector and along the skin of the patient providing a fairly light-tight area around the whole optical thermodetector. The removable handle (not shown) is then attached to the top of rod 18. Before the test takes place, the film must be ready for exposure. Film cover 92 is then removed from cartridge 24 by pulling tab 100. LED 40 should be in the on condition. A skilled technician then initiates the test by placing one hand on the top of cartridge 24 to hold it down on the skin of the patient. With the other hand the technician will pull outwardly in the direction C on the handle of rod 18. This pulls rod 18, case 12, and needle 14 upwardly in the direction of arrow C. The speed of the pull by the technician determines the extent of the exposure of the film. As the needle is being withdrawn the viewing point 64 of optical fibers passes by the tissue to be tested. As well, resistor 44 and thermistor 46 pass along the tissue to be tested sensing the temperature. As this is occurring, slit 102 of LED 40 and slits 80 pass along the film plane 58. The light projected from the LED 40 and that conducted by optical fibers 66 and 68 are projected onto film 90 residing in film plane 58 as the instrument assembly 11 is being drawn upwardly.

When needle 14 has been completely withdrawn from the patient, top seal 26 and cartridge 24 may be removed and the needle 14 and instrument assembly 11 pulled completely away from cartridge 24 while retaining a light-tight seal on the bottom of cartridge 24 and maintaining the shroud 88 completely around cartridge 24. Diaphragm 28 is then closed to reduce any chance of light leakage into the lower portion of cartridge 24. The top should still be kept light-tight by the shroud. At this time the tab 98 of film 90 may be pulled to initiate the development of the film and to pull the film out of cartridge 24. Once this has been done there is no longer any need for a light-tight cover or compartment. If normal film is used which needs to be developed separately, at this point, that film may be removed and placed in a light-tight container for development at a later time.

It should be noted that because thermistor 46 cannot be located at the same level as point 64 where the fibers exit from needle 14, the difference, distance d, is compensated for inside of case 12. The difference in the level between slit 102 and slits 80 is made to be the same distance d. The correction allows the temperature information on the film to correspond directly to the optical information without any need for further correction factors to be used by the technician.

A sample film resulting from the above described operation is illustrated in FIG. 4. The information is recorded in three columns 108, 110 and 112. Column 112 represents the LED. Column 110 represents the image from the light fiber having its tip upward, that is, away from the skin of the patient. Column 108 represents the image from the optical fiber having its base upward. Therefore column 110 would relate to fiber 66 and column 108 would relate to fiber 68. In FIG. 4, the arrow H designates direction away from the skin in the direction of withdrawal of needle 14 and G designates the direction towards the skin of the patient. In the sample illustration of the film, level A illustrates the lower surface of a layer of tissue and level B illustrates the upper surface of that same layer of tissue. Additionally, level B also indicates the lower surface of the next layer of tissue with its upper surface at level C. It can be seen that the same procedure continues on up through level F. Tissue between level C and F has a higher basal temperature than the rest of the tissue, as seen in column 112. That is, when the tissue is at its normal reference temperature, LED 40 remains on, thereby exposing column 112 with its light (in this case, orange light is represented). When the temperature rises sufficiently above the reference temperature, LED 40 goes out, leaving the film black. Black (unexposed) portions of the film are shown by shading designated by reference numerals 109. After the test has been made, the needle is placed in a water bath with a digital readout which is then regulated to determine what the actual reference temperature was. This can then be recorded as shown on the edge of the sample film as shown at 111. The changes between different layers of tissue, which have different colors, can be recognized in the sample film by the abrupt change in color. An abrupt change in color will occur when the base of the triangular cross section of the optical fiber crosses from one color into another. The crossing of the point of a fiber from one color to another will be represented on the film by a gradual change in color.

A second embodiment of the instant invention can be seen in FIG. 5. The device of FIG. 5 uses the temperature element of the instant invention housed inside a smaller housing than the embodiment shown in FIG. 1. The thermodetector of FIG. 5 is adapted for use, as described above, as an instrument to determine the time of ovulation for a woman. The thermodetector has a housing 114. Many of the components included within housing 114 are identical to those used in the optical thermodetecter of FIG. 1. Those identical parts will maintain the same reference numerals as in FIG. 1. Housing 114 has a cylinder 116 projecting therefrom. The cylinder 116, which would most likely be made of nickel but could also be made of other material as well, is hollow to encase electronics at the end 118. Resister 44 and thermistor 46 are located near end 118. End 118 is adapted to be inserted internally, either orally, vaginally or rectally in the woman checking her temperature. Wires 42 connect resistor 44 and thermistor 46 to the electronics module 32. Electronics module 32 is also operatively connected to battery 34, switch 48, variable resistor 36 and LED 40. The circuit for operating this and the temperature element of FIG. 1 is disclosed in FIG. 6. It should be noted here that the unit is stored with the battery in the off position by switch 48. When the temperature is being taken, the LED is placed so that it can be observed externally. In one mode of operation, the LED is glowing when basal temperature is at or below that of ovulation. If the LED goes off after insertion, this indicates that ovulation temperature has been reached. On removal of the device from the orifice tested, the LED should go back on verifying the temperature difference. If the LED does not go back on, the battery should be checked. The variable resistor 36 is set using adjusting screw 37 by a qualified physician or technician at the basal temperature of the woman. It is then sealed so that it may not be altered during use.

In another mode of operation, the circuit may be tailored such that the LED is off at the basal temperature and at 0.4° F. above the basal temperature the LED comes on. Between those two temperatures the LED flashes on and off. The circuit in FIG. 6 will be described in connection with this mode of operation.

The actual sensing element is thermistor 46 and resistor 44 both located in box 124; they make up the sensor of this thermodetector. Both thermistor 46 and resistor 44 must remain at approximately the same temperature when a measurement is taken to ensure that the reading is independent of ambient temperatures which may vary between 50° F. and 100° F. A thermistor is chosen for this purpose over other sensing devices because of its high sensitivity, stability, and low cost. Thermistor non-linearity is not a problem because of the narrow temperature range, generally between 97° F. and 99° F. used in this thermodetector. However, to ensure long term stability thermistor 46 and resistor 44 must be sealed against moisture and protected against mechanical stress. For that reason the thermistor 46 and resistor 44 will usually be embedded in some type of heat conductive epoxy filling cylinder 116. This also applies for the resistor 44 and thermistor 46 as disclosed in FIG. 1; the needle will be filled with some type of heat conductive epoxy or the like to protect the components therein. The thermistor 46 is connected into a bridge circuit in order to convert its variable resistance into a temperature dependent voltage which appears between points 126 and 128 of the circuit, this is at the entrance to integrated circuit (IC) 130. The bridge is balanced for any given reference temperature by adjusting variable resistor 36. When the bridge is balanced, that is, the temperature equivalent voltage at point 126 being equal to that at point 128, the output at point 132 of IC 130 is zero. Capacitor 134 serves to filter bridge noise and any noise pick-up from power lines. IC 130 (LM10CLN) is a combination voltage reference and operational amplifier on the same monolithic chip. IC 130 will operate on voltages as low as 1.5 Volts while having low drift and low power consumption. The voltage reference supplies a constant 2.2 Volts to power the bridge at point 136. This voltage is highly regulated and is therefore insensitive to changes in battery voltage. The 2.2 Volt reference voltage also appears at point 137.

Ignoring IC 138 for the moment, the circuits works as follows. The slightest bridge imbalance caused by the temperature going above the reference temperature set at variable resistor 36, is amplified about 400,000 times by the operational amplifier contained in IC 130. Its output which appears at point 132 goes positive, which turns on transistor 140, which therefore conducts between point 142 and ground, thereby illuminating LED 40. Likewise, by lowering the temperature below the reference temperature, the LED goes off. Transistor 140, also serves to prevent excess current from being supplied by IC 130. Such current can create "thermal feedback" inside IC 130, thus reducing the accuracy of the circuit.

IC 138, contains three voltage controlled SPDT switches. Two of the switches are wired to act as inverters which are connected form a low frequency oscillator. The third switch is used as a switch driven by the output of the of the oscillator. As such it switches point 144 between ground and 2.2 Volts. This highly stable square wave is reduced by a voltage divider of resistor 148 and 150 and applied to point 152 of IC 130. Point 152 of IC 130 provides offset adjustment for the operational amplifier. When a voltage is applied to this point, the increase in the amplifier offset voltage means that the bridge must be unbalanced by a slightly higher temperature in order to turn on LED 40. This offset is chosen to correspond to a temperature change of approximately 0.4° F. or 0.5° F. depending on the voltage divider resistor 148. Therefore when the temperature is slightly above the set point the LED blinks on and off as the offset voltage changes according to the oscillating frequency. However as the temperature is increased further the bridge output voltage exceeds the offset voltage and so the LED stays on continuously. When the temperature is below the set point, the LED is always off. Note that resistors 150 (all four of them) in this circuit are disposed on a single chip. They are called tracking resistors because their resistance change with the temperature is the same for all four resistors. By means of their tracking each other and their placement in the circuit, their changes in resistance have no effect on the reference temperature set.

The other modes of operation can be accommodated very easily using the same circuit with only minor modifications. The circuit is powered by battery source 34 and switch 48 and applies power to the circuit. By the simple expedient of eliminating IC 138 the flashing on and off of the LED may be eliminated. Additionally, a small change, such as an inverter between point 132 and transistor 140, would alter the circuit such that the LED is on at the reference temperature and goes off when the temperature rises (as shown in the operation of the embodiment of FIG. 1).

Figure 6:
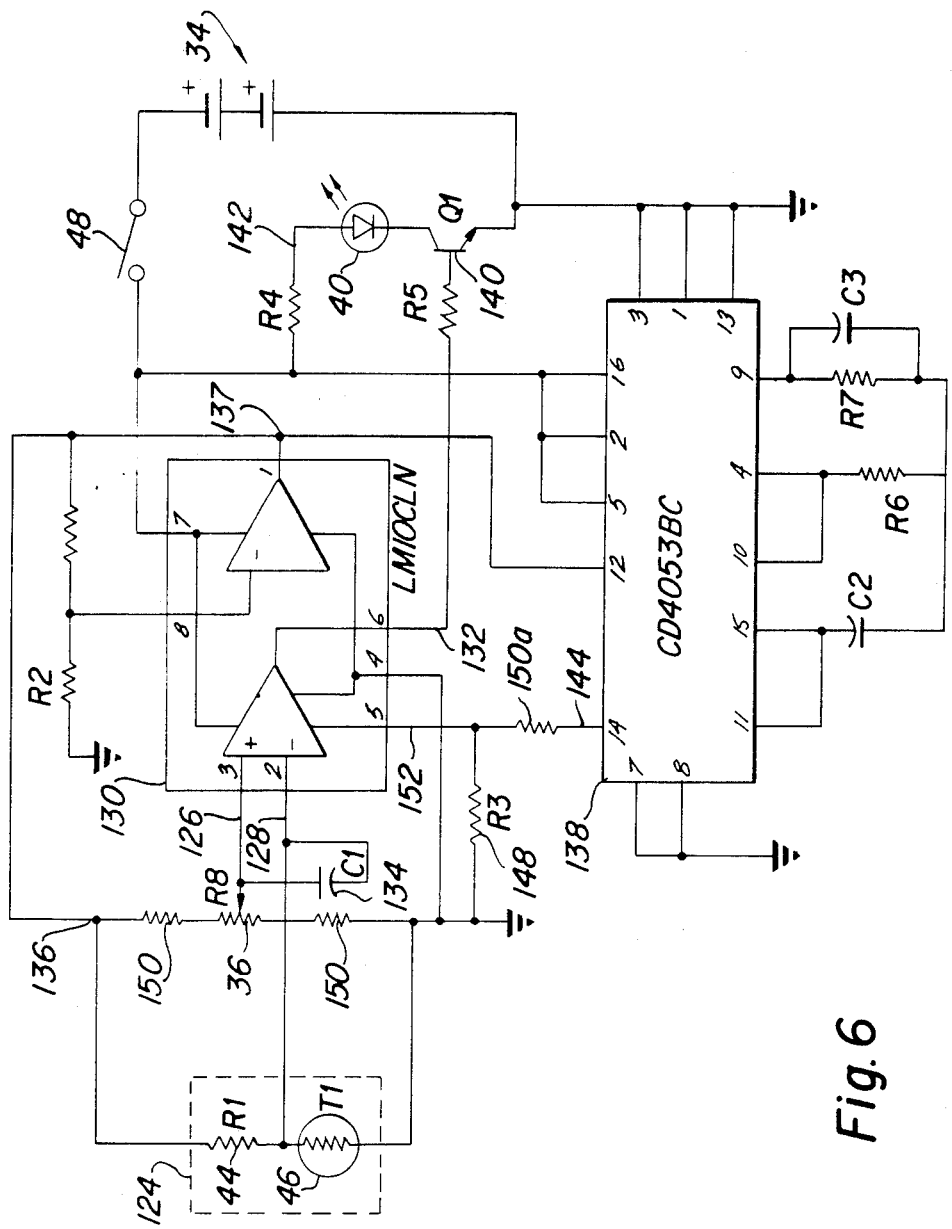
FIG. 6 is schematic diagram of the electronic circuit of the temperature element employed in both embodiments of this invention.

A further embodiment of the instant invention can be employed using the thermodetector of FIG. 5 having three different circuits of the type disclosed in FIG. 6. Each different circuit would have its reference temperature set at a different point. For example, one circuit may be set on basal temperature during the estrogen dominated period of the cycle, a second circuit will be set 0.1° F. less than the ovulation temperature and a third set at the ovulation temperature, using three different colored LED's, one for each circuit, and patterned to indicate temperature raise. It is possible that other temperatures may be set at the reference temperature for different uses of this device.

The insertion end 118 of the embodiment disclosed in FIG. 5, may be flat so that it is easily adaptable to be held under the tongue, back against the base. This device allows readings to be essentially instantaneous because the response time for the circuit is in milliseconds.

While the instant invention has been described in several embodiments, this description is not intended to limit the scope of this invention to those embodiments. Other embodiments may still be within the scope of the claims below. It is contemplated that the thermodetector of FIG. 5 could also be constructed such that instead of an LED for the indicating means, a transducer which gives an auditory or tactile signal, indicting a change from the reference temperature, could be employed. It is also contemplated that the indicator output could be used to drive a strip chart recorder or other type device for automatic data collection, or to influence the operation of another circuit.

We claim:

1. An optical-thermodetector for testing tissue, comprising:
    (a) a housing including a case and a needle-like extension projecting therefrom, said extension having a sharp end for piercing the skin of a patient;
    (b) a temperature element disposed within said housing and having indicating means responsive to a predetermined change in temperature, said temperature element including sensor means disposed near the end of said needle-like extension; and
    (c) an optical element disposed within said housing for recording the coloration of the tissue from an area near said temperature sensor, said optical element comprising:
        (i) a light source;

(ii) an incident light path for conducting light from said source to the tissue to be tested;
(iii) a light collector disposed within said case;
(iv) a reflected light path for conducting reflected light from said tissue to said collector and
(v) a film plane, where film for recording tissue coloration is to be located, said film plane being moveable with respect to said light collector, said collector projecting light from said reflected light path onto said film plane.

2. The optical thermodetector of claim 1, wherein said film plane is contained in a cartridge which is detachable from said housing.

3. The optical thermodetector of claim 1, wherein said indicating means emits light.

4. The optical thermodetector of claim 3, wherein said optical element also records the status of whether said indicating means is illuminated or not.

5. The optical thermodetector of claim 4, wherein the recording of the status of the indicating means corresponds to the recording of the coloration of tissue for the same depth of tissue tested.

6. The optical thermodetector of claim 1, wherein said incident and reflected light paths include optical fibers.

7. The optical thermodetector of claim 6, wherein said optical fibers are triangular in cross-section.

8. The optical thermodetector of claim 7, wherein the optical fibers of said incident and said reflected light path are formed together in a bundle of four optical fibers, said fibers being light insulated from each other.

9. The optical thermodetector of claim 8, wherein the optical fibers in said fiber bundle are arrayed such that the base of a triangular cross-section of a fiber is adjacent the tip of the triangular cross-section of its adjacent fiber.

10. The optical thermodetector of claim 9, wherein said light collector is a lens to focus light from said optical fibers onto said film plane.

11. The optical thermodetector of claim 10, wherein said lens is generally disc-like in shape and having an opaque coating except for apertures on the edge thereof, for incoming light from said reflected light path and an outgoing aperture for outgoing light to said film plane, and said outgoing aperture is adjacent said film plane.

12. The optical thermodetector of claim 11, wherein said lens is thick enough to receive the optical fibers at said incoming aperture but much thinner at said outgoing aperture.

13. The optical thermodetector of claim 6, wherein said temperature element also includes,
means for setting a reference temperature,
means for detecting a predetermined change in temperature from said reference temperature, and
means operatively connecting said detecting means with said indicating means for energizing said indicating means in response to said predetermined change in temperature.

14. The optical thermodetector of claim 13, wherein said detecting means is capable of detecting a change of at least 0.1° F.

15. The optical thermodetector of claim 13, wherein said detecting means includes a resistor and a thermistor located in close proximal relationship to each other.

16. The optical thermodetector of claim 14 or 15, wherein the indicating means includes a light emitting diode which is illuminated upon the energizing of said indicating means.

* * * * *